US012624905B2

(12) United States Patent
Jiang et al.

(10) Patent No.: US 12,624,905 B2
(45) Date of Patent: May 12, 2026

(54) END PRODUCT FOR AIR-CONDITIONING INDOOR UNIT AND AIR-CONDITIONING INDOOR UNIT

(71) Applicant: Carrier Corporation, Palm Beach Gardens, FL (US)

(72) Inventors: Qiwen Jiang, Shanghai (CN); Zhiwang Guo, Shanghai (CN); Hongsheng Liu, Shanghai (CN); Yinbo Rui, Shanghai (CN); Yihu He, Shanghai (CN); Chao Ding, Shanghai (CN); Michael Birnkrant, Palm Beach Gardens, FL (US); Peter J. Mckinney, Palm Beach Gardens, FL (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 111 days.

(21) Appl. No.: 18/406,954

(22) Filed: Jan. 8, 2024

(65) Prior Publication Data

US 2024/0230244 A1     Jul. 11, 2024

(30) Foreign Application Priority Data

Jan. 9, 2023   (CN) .......................... 202310030263.6

(51) Int. Cl.
*F28D 1/04*      (2006.01)
*A61L 2/00*      (2006.01)
*F28F 1/32*      (2006.01)

(52) U.S. Cl.
CPC ............ *F28F 1/325* (2013.01); *A61L 2/0047* (2013.01); *A61L 2202/11* (2013.01); *F28F 2245/02* (2013.01)

(58) Field of Classification Search
CPC ..... F28F 1/325; F28F 2241/02; A61L 2/0047; A61L 2202/11
USPC ......................................... 165/151
See application file for complete search history.

(56) References Cited

FOREIGN PATENT DOCUMENTS

| CN | 112789173 | A | * | 5/2021 | ................ | C08J 5/18 |
|----|-----------|---|---|--------|----------------|-----------|
| JP | H10103885 | A | * | 4/1998 | | |
| JP | 2934916 | B2 | * | 8/1999 | | |
| JP | 6656785 | B1 | * | 3/2020 | | |
| JP | 112789173 | A | * | 5/2021 | | |

* cited by examiner

*Primary Examiner* — Davis D Hwu
(74) *Attorney, Agent, or Firm* — Drew Folgmann

(57) ABSTRACT
The invention relates to an end product for air-conditioning indoor unit, which comprises a heat exchange tube through which air and refrigerant exchange heat; a heat exchange fin on which a tube hole for passing through the heat exchange tube is formed and the surface of which is coated with a hydrophilic coating containing photocatalytic material; and an ultraviolet lamp arranged at or near the heat exchange fin, so that the ultraviolet light of the ultraviolet lamp can cover the surface of the heat exchange fin coated with the hydrophilic coating. The invention further provides an air-conditioning indoor unit configured with the end product and a method for coating heat exchange fins of the end product. The end product for air-conditioning indoor unit according to the invention can achieve highly efficient air purification.

18 Claims, 2 Drawing Sheets

110

131

110

120

END PRODUCT FOR AIR-CONDITIONING INDOOR UNIT AND AIR-CONDITIONING INDOOR UNIT

CROSS REFERENCE TO RELATED APPLICATION

This application claims priority to Chinese Patent Application No. 202310030263.6 filed on Jan. 9, 2023, which is incorporated by reference herein in its entirety.

FIELD OF THE INVENTION

The invention relates to the technical field of air conditioning, in particular to an end product for air-conditioning indoor unit, and also relates to an air-conditioning indoor unit configured with the end product and a method for coating heat exchange fins of the end product.

BACKGROUND OF THE INVENTION

With the advancement of science and technology and development of economy, people's quality of life has been continuously improved, and people begin to pay more attention to their own quality of life. Air conditioner, as a product that can improve people's indoor comfort, has been installed in more and more buildings in recent decades. Air conditioners help people solve the problem of indoor thermal comfort, in recent years, however, more and more attention has been paid to the issue of indoor air quality.

In recent years, with the deterioration of air quality, the content of air pollutants keeps soaring, which leads to the deterioration of air quality both indoors and outdoors, thus bringing great troubles to people's life. Since 2020, the COVID-19 pandemic worldwide has caused serious harm to human health and social economy. The virus is transmitted mainly by close person-to-person contact via droplets or skin touch. Therefore, how to efficiently eliminate viruses and bacteria has attracted great attention from all over the world. At present, many air conditioners on the market have certain air purification capabilities, for example, larger particles can be filtered and adsorbed by means of filter screens. However, these filter materials are only limited to the elimination of particulate pollutants, that is, adsorption and filtration of particles or molecules of their corresponding diameters. The selectivity to adsorbates is too high to be used alone in complex gas environments. For example, it is difficult for filter screens to eliminate biological pollutants such as bacteria and viruses. Unsterilized gases may carry bacteria, viruses, carcinogen carriers, etc., which, once invade human lungs, will seriously endanger human health. In addition, other gas purification devices, commonly known as "ion generators", are designed to emit negative ions into the surrounding air. These ions adhere to positively charged pollutants such as particles or dust, causing the pollutants to become heavy and fall or become precipitated or trapped in the collection plate. However, ion generators cannot effectively eliminate chemical pollutants, such as volatile organic compounds (VOCs) in the air environment. For example, the existing air-conditioning indoor unit can use ultraviolet photocatalytic oxidation technology for sterilization, but it is difficult to achieve rapid sterilization due to the limited photocatalytic contact area. How to improve the sterilization efficiency of ultraviolet photocatalysis has always been the focus of attention.

Therefore, there is an urgent need to provide an end product for air-conditioning indoor unit that can achieve efficient air purification.

SUMMARY OF THE INVENTION

In view of the above, according to a first aspect of the invention, an end product for air-conditioning indoor unit is provided, which effectively solves the aforementioned problems and problems in other aspects existing in the prior art. The end product for air-conditioning indoor unit according to the invention comprises:

a heat exchange tube, through which air and refrigerant exchange heat;

a heat exchange fin, on which a tube hole for passing through the heat exchange tube is formed, and a surface of which is coated with a hydrophilic coating containing photocatalytic material; and an ultraviolet lamp arranged at or near the heat exchange fin so that ultraviolet light of the ultraviolet lamp covers the surface of the heat exchange fin coated with the hydrophilic coating.

In another embodiment of the end product according to the invention, the photocatalytic material is selected from one or more of titanium dioxide, silicon dioxide, zinc oxide or tungsten trioxide.

In yet another embodiment of the end product according to the invention, the hydrophilic coating has a thickness in the range of 0.5-20 mm and a material density of 0.02-1.0 $g/m^3$.

In still another embodiment of the end product according to the invention, the ultraviolet lamp is arranged upstream and/or downstream of the heat exchange fin in the direction of air flow.

In a further embodiment of the end product according to the invention, the distance between the ultraviolet lamp and the heat exchange fin is in the range of 200-900 mm.

In another embodiment of the end product according to the invention, a plurality of ultraviolet lamps are provided, the plurality of ultraviolet lamps having the same size and being arranged at equal intervals in the length direction of the heat exchange tube, wherein the distance covered by the ultraviolet light of a single ultraviolet lamp in the length direction of the heat exchange tube is twice the distance between the single ultraviolet lamp and the heat exchange fin.

In yet another embodiment of the end product according to the invention, the ultraviolet lamp is a spotlight and is arranged at the top and/or bottom of the heat exchange fin.

In still another embodiment of the end product according to the invention, the ultraviolet lamp has a long strip-shaped tubular body that is arranged between two adjacent heat exchange tubes and installed in the tube hole of the heat exchange fin.

In a further embodiment of the end product according to the invention, the hydrophilic coating covers all or part of the surface of the heat exchange fin.

In another embodiment of the end product according to the invention, a plurality of heat exchange fins are provided, wherein the plurality of heat exchange fins are parallel to each other and arranged at intervals.

In yet another embodiment of the end product according to the invention, the air-conditioning end product is a fan-coil unit or a combined air-conditioning unit.

In addition, according to a second aspect of the invention, an air-conditioning indoor unit is further provided, wherein the air-conditioning indoor unit comprises the aforementioned end product connected by pipes.

Furthermore, according to a third aspect of the invention, a method for coating heat exchange fins of the aforementioned end product is further provided, the method comprising:

applying a hydrophilic coating containing photocatalytic material to the surface of the heat exchange fin by roll-coating, and curing the hydrophilic coating at a temperature of 120-300° C.

The end product according to the invention advantageously combines heat exchange fins with the photocatalytic device for use in an air-conditioning indoor unit, so that in addition to regulating the temperature and humidity of indoor air, the air-conditioning indoor unit can also eliminate chemical and biological pollutants, thereby enhancing sterilization and disinfection effects and significantly improving air quality.

BRIEF DESCRIPTION OF THE DRAWINGS

The technical solutions of the invention will be described in further detail below in conjunction with the accompanying drawings and embodiments, where.

DETAILED DESCRIPTION OF EMBODIMENT(S) OF THE INVENTION

Some embodiments of the invention will be described in detail below with reference to the accompanying drawings. It should be noted that orientation terms such as upper, lower, left, right, front, rear, inner side, outer side, top, bottom, upstream and downstream mentioned or possibly mentioned in this specification are defined relative to the configurations illustrated in the respective drawings. They are relative concepts, so they may change accordingly according to their different locations and different states of use. Therefore, these and other orientation terms shall not be construed as restrictive terms.

The effective treatment of air pollution, especially indoor air pollution, which causes serious harm to human body, has attracted more and more attention. Hundreds of volatile organic compounds (VOCs) have been identified from indoors, mainly including aromatic hydrocarbons, chlorinated hydrocarbons, aldehydes and ketones. With pandemic worldwide of the COVID-19, it is imperative to improve indoor air quality. According to the principle of action, the methods for indoor air purification used by air-conditioning indoor units currently on the market can be divided into ventilation type, filter type, adsorption type and catalytic purification type, etc., but they all have their own shortcomings. The air conditioner can regulate the temperature and humidity of the indoor air but cannot improve the air quality. The ion generator cannot decompose chemically harmful substances. The filter device can adsorb particles and dust, is limited by the saturated adsorption capacity and thus needs to be replaced frequently, and the filter material needs further treatment after adsorption. The ultraviolet lamp can be used for sterilization and disinfection, but cannot degrade volatile organic compounds.

Figure 1:
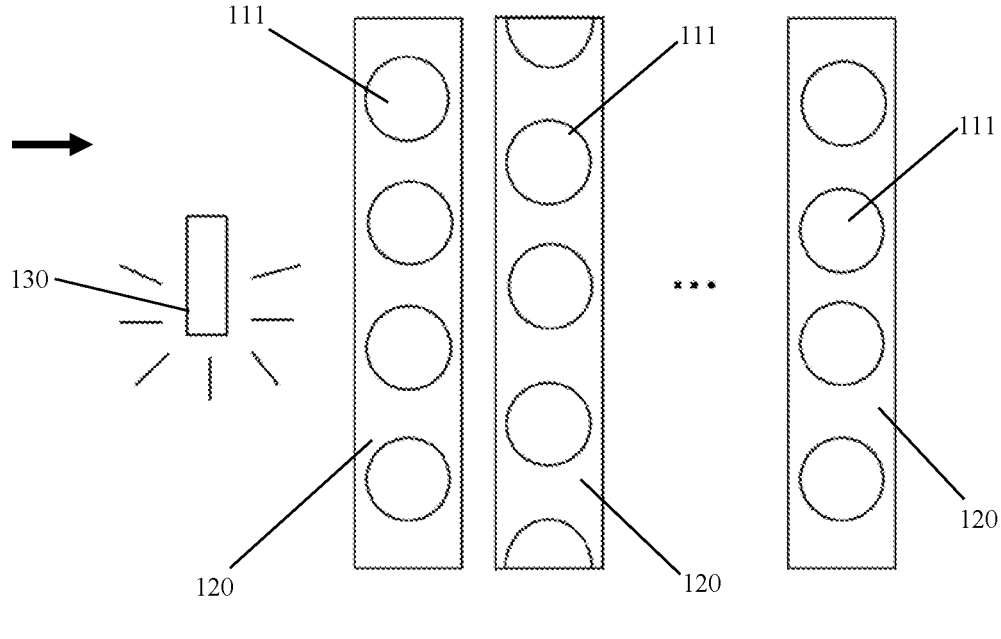
FIG. 1 is a structural schematic diagram of the end product for air-conditioning indoor unit according to the invention being applied in the air-conditioning indoor unit viewed from the side.

As shown in FIG. 1, it schematically illustrates in general the structure of an embodiment of an end product for air-conditioning indoor unit according to the invention. As can be explicitly seen from FIG. 1, the end product mainly consists of heat exchange tubes 110, heat exchange fins 120, ultraviolet lamps 130 and other components. It is well known to those skilled in the art that, air and refrigerant exchange heat through the heat exchange tubes 110. It should be noted that the heat exchange tube of the end product for air-conditioning indoor unit of the invention refers to the tube which allows the indoor air and the refrigerating medium inside the tube (in most cases cooling water but may also be water solutions of organic compounds such as glycol or glycerol) to exchange heat but is not limited to the tube referred to in the context. In addition, the heat exchange tube 110 can be one of aluminum pipe, copper pipe or steel pipe with a circular, square or elliptical cross section shape etc. Therefore, the shape and material of the heat exchange tube 110 can be selected according to different working environments or requirements. With continued reference to FIG. 1, tube holes 111 are formed on the heat exchange fins 120 for passing through the heat exchange tubes 110. There may be a plurality of heat exchange fins 120, which are parallel to each other and arranged at intervals of a certain distance. The surface of the heat exchange fin 120 is coated with a hydrophilic coating containing photocatalytic material such as titanium dioxide, silicon dioxide, zinc oxide, copper oxide, cadmium sulfide, aluminum oxide or tungsten trioxide, etc. The ultraviolet lamp 130 is arranged at or near the heat exchange fin 120 so that the ultraviolet light of the ultraviolet lamp 130 can cover the surface of the heat exchange fin 120 coated with the hydrophilic coating. Under the irradiation of the ultraviolet lamp, the electrons of the photocatalytic material jump from the valence band to the position of the conduction band, forming photoelectrons in the conduction band, thus forming electron-hole pairs. These electron-hole pairs, after reacting with the surrounding water or oxygen, can decompose pollutants such as formaldehyde and benzene in the air into harmless substances, and can also destroy the cell wall to achieve sterilization and bacteriostatic effects.

It should be emphasized that the hydrophilic coating on the surface of the heat exchange fin 120 has extremely strong hydrophilicity and self-cleaning ability. Specifically, water droplets will usually condense on the outer surface of the heat exchange fin 120, and the condensed water droplets can wash away dust, impurities or other pollutants deposited on the surface of the heat exchange fin 120, allowing the hydrophilic coating to enhance both light utilization and photocatalytic activity.

It is easy for those skilled in the art to understand that the thickness of the hydrophilic coating can be configured in the range of 0.5-20 mm, and the material density of the hydrophilic coating is 0.02-1.0 $g/m^3$. It is easy to understand that the hydrophilic coating can be coated on one or both sides of the heat exchange fin 120 as required. Further, the hydrophilic coating can cover all or part of the surface of the heat exchange fin 120. For example, the hydrophilic coating covers one-half or one-third of the surface of the heat exchange fin 120 closer to the ultraviolet lamp 130, so as to save manufacturing costs.

Figure 2:
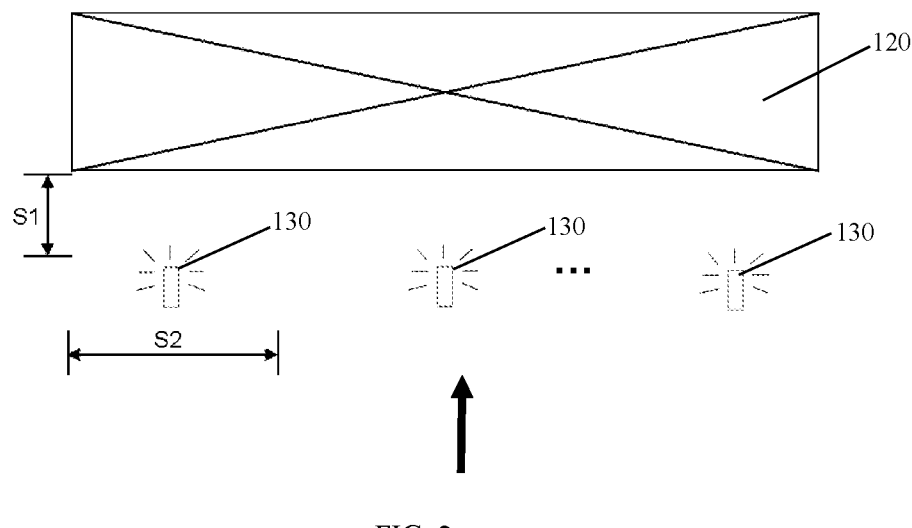
FIG. 2 is a structural schematic diagram of the end product for air-conditioning indoor unit according to the invention being applied in the air-conditioning indoor unit viewed from the top.

In conjunction with other preferred embodiment in the above embodiments, the ultraviolet lamp 130 may be arranged upstream of the heat exchange fin 120 in the direction of air flow (as shown by the arrow in FIG. 1). Of course, the ultraviolet lamp 130 can also be arranged downstream of the heat exchange fin 120 in the direction of air flow. Further, the distance between the ultraviolet lamp 130 and the heat exchange fin 120 is in the range of 200-900 mm. As shown in FIG. 2, there are a plurality of ultraviolet lamps 130, which have the same size and are arranged at equal intervals in the length direction of the heat exchange tube 110, where the distance S2 covered by the ultraviolet light of a single ultraviolet lamp 130 in the length direction of the heat exchange tube 110 is twice the distance S1 between the single ultraviolet lamp 130 and the heat exchange fin 120.

Figure 3:
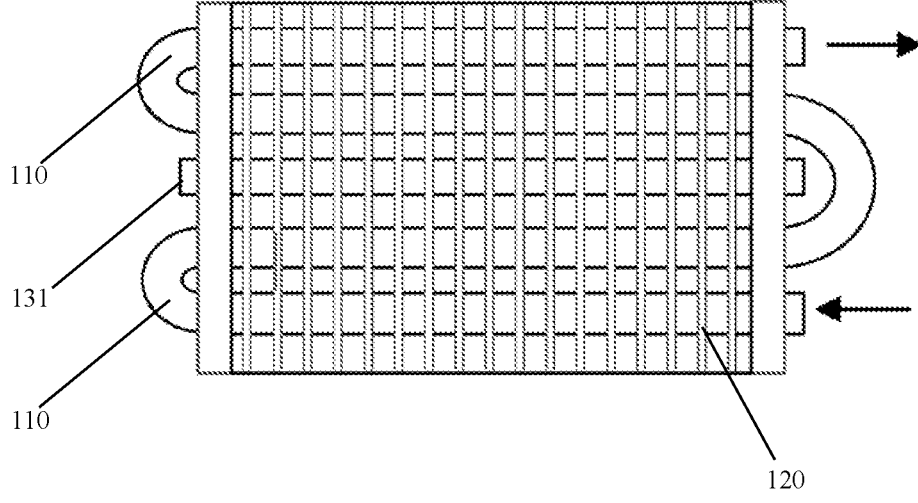
FIG. 3 is a structural schematic diagram of an ultraviolet lamp of the end product for air-conditioning indoor unit according to the invention installed in a heat exchange tube.

As an alternative, the ultraviolet lamp may take the form of a spotlight and be arranged at the top and/or bottom of the heat exchange fin 120. By direct irradiation, ultraviolet light can be focused on the hydrophilic coating with photocatalytic material of the heat exchange fin 120, thus obtaining better photocatalytic effect. In addition, as an alternative, the ultraviolet lamp can be designed as a long strip-shaped tubular body 131, which is arranged between two adjacent heat exchange tubes 120 and installed in the tube holes 111 of the heat exchange fins 120, as shown in FIG. 3. The photocatalytic material can perform a photocatalytic reaction under the irradiation of the ultraviolet light in UVC band, so as to oxidize organic volatile gas in air into harmless substances. At the same time, the photocatalytic material will generate active free radicals under the irradiation of ultraviolet light, which can kill some germs with nucleus or membrane that are difficult to kill by ultraviolet light alone. Under the strong oxidation of active free radicals, the cells are directly destroyed, causing the microbial components such as protein, nucleic acid and lipids of the germs to be oxidized into $CO_2$ and $H_2O$, so that they cannot be regenerated at all, thus completely achieving the purpose of killing bacteria.

In some embodiments, the air-conditioning end product is a fan-coil unit or a combined air conditioning unit. Taking the fan-coil unit as an example, the indoor unit of the air-conditioning indoor unit comprises a housing (not shown) having an air inlet end and an air outlet end. The air inlet end is configured to receive ambient air and the air outlet end is configured to deliver purified air into the interior space. The housing provides a flow path from the air inlet end to the air outlet end. The indoor unit of the air-conditioning indoor unit further comprises a fan and a drive mechanism. The end product is arranged in the flow path for eliminating ambient gas pollutants passing through it.

In addition, the invention also provides an air-conditioning indoor unit including the aforementioned end product. It can be understood that in addition to the conventional function of cooling or heating, the air-conditioning indoor unit equipped with the aforementioned end product also has the function of high-efficiency air purification.

Furthermore, the invention further proposes a method for coating heat exchange fins of the aforementioned end product, which at least comprises two method steps:

Step 1: applying a hydrophilic coating containing photocatalytic material to the surface of the heat exchange fin 120 by roll-coating, and Step 2: curing the hydrophilic coating at a temperature of 120-300° C.

It can be seen that the photocatalytic material of the invention can be directly added to the hydrophilic layer to fabricate a hydrophilic coating with photoinduced property. The method steps are simple and easy to operate. The hydrophilic membrane fabricated has highly efficient antibacterial and formaldehyde removal abilities, so as to continuously protect the health of the people indoors.

In summary, the end product for air-conditioning indoor unit according to the invention advantageously combines heat exchange fins with ultraviolet lamps using photocatalysis, which can not only increase the area for photocatalytic reaction to further improve air purification efficiency, but also eliminate chemical and biological pollutants to further enhance the sterilization and disinfection effects.

Some specific embodiments are listed above to illustrate in detail the end product for air-conditioning indoor unit, the air-conditioning indoor unit equipped with the end product, and the method for coating heat exchange fins of the end product according to the invention. These individual examples are only used to illustrate the principle of the invention and the implementations thereof, but not to limit the invention. Those skilled in the art may without departing from the spirit and scope of the invention, make various modifications and improvements. Therefore, all equivalent technical solutions shall belong to the scope of the invention and be defined by the various claims of the invention.

What is claimed is:

1. An end product for an air-conditioning indoor unit, comprising:

a heat exchange tube, through which air and refrigerant exchange heat;

a heat exchange fin, on which a tube hole for passing through the heat exchange tube is formed, and a surface of which is coated with a hydrophilic coating containing photocatalytic material;

an ultraviolet lamp arranged at or near the heat exchange fin, so that ultraviolet light of the ultraviolet lamp covers the surface of the heat exchange fin coated with the hydrophilic coating;

wherein the ultraviolet lamp is arranged upstream and/or downstream of the heat exchange fin in a direction of air flow; and wherein a plurality of ultraviolet lamps are provided, the plurality of ultraviolet lamps having the same size and being arranged at equal intervals in a length direction of the heat exchange tube, wherein a distance covered by ultraviolet light of a single ultraviolet lamp in the length direction of the heat exchange tube is twice a distance between the single ultraviolet lamp and the heat exchange fin.

2. The end product according to claim 1, wherein the photocatalytic material is selected from one or more of titanium dioxide, silicon dioxide, zinc oxide or tungsten trioxide.

3. The end product according to claim 2, wherein the hydrophilic coating has a thickness in a range of 0.5-20 mm and a material density of $0.02-1.0 \ g/m^3$.

4. The end product according to claim 1, wherein the distance between the ultraviolet lamp and the heat exchange fin is in a range of 200-900 mm.

5. The end product according to claim 1, wherein the ultraviolet lamp is a spotlight and is arranged at the top and/or bottom of the heat exchange fin.

6. The end product according to claim 1, wherein the ultraviolet lamp has a long strip-shaped tubular body that is arranged between two adjacent heat exchange tubes and installed in a tube hole of the heat exchange fin.

7. The end product according to claim 1, wherein the hydrophilic coating covers all or part of the surface of the heat exchange fin.

8. The end product according to claim 1, wherein a plurality of heat exchange fins are provided, the plurality of heat exchange fin being parallel to each other and arranged at intervals.

9. The end product according to claim 1, wherein the air-conditioning end product is a fan-coil unit or a combined air-conditioning unit.

10. An air-conditioning indoor unit, wherein it comprises the end product according to claim 1 connected by pipes.

11. A method for coating heat exchange fins of the end product according to claim 1, wherein it comprises:

applying a hydrophilic coating containing photocatalytic material to the surface of the heat exchange fin by roll-coating, and curing the hydrophilic coating at a temperature of 120-300° C.

12. A method, comprising:

arranging one or more ultraviolet lamps at or near a heat exchange fin and a heat exchange tube, the heat exchange fin comprising a surface coated with a photocatalytic material, such that ultraviolet light of the one or more ultraviolet lamps covers the surface; and irradiating the photocatalytic material with the one or more ultraviolet lamps.

13. The method according to claim 12, wherein the one or more ultraviolet lamps includes a plurality of ultraviolet lamps arranged at or near the heat exchange fin.

14. The method according to claim 13, wherein the plurality of ultraviolet lamps have the same size and are arranged at equal intervals in a length direction of the heat exchange tube.

15. The method according to claim 12, wherein a distance covered by ultraviolet light of the one or more ultraviolet lamps in a length direction of the heat exchange tube is twice a distance between the one or more ultraviolet lamps and the heat exchange fin.

16. The method according to claim 12, wherein the one or more ultraviolet lamps are arranged upstream and/or downstream of the heat exchange fin in a direction of airflow.

17. The method according to claim 12, wherein a distance between the one or more ultraviolet lamps and the heat exchange fin is in a range of 200-900 mm.

18. The method according to claim 12, wherein photocatalytic material is selected from one or more of titanium dioxide, silicon dioxide, zinc oxide or tungsten trioxide.

* * * * *